United States Patent [19]
Pagedas

[11] Patent Number: 5,413,585
[45] Date of Patent: May 9, 1995

[54] SELF LOCKING SUTURE LOCK

[76] Inventor: Anthony C. Pagedas, 8401 W. Edgerton, Greendale, Wis. 53129

[21] Appl. No.: 995,104

[22] Filed: Dec. 22, 1992

[51] Int. Cl.⁶ .......................................... A61B 17/04
[52] U.S. Cl. .................................. 606/232; 606/151
[58] Field of Search ............. 606/151, 157, 158, 219, 606/220, 228, 232; 227/902; 24/16 PB

[56] References Cited

U.S. PATENT DOCUMENTS

| | | | |
|---|---|---|---|
| 3,409,014 | 11/1968 | Shannon | 606/148 |
| 4,580,319 | 4/1986 | Paradis | 24/16 PB |
| 4,598,708 | 7/1986 | Beranek | 606/157 |
| 4,611,593 | 9/1986 | Fogarty et al. | 606/158 |

FOREIGN PATENT DOCUMENTS

| | | | |
|---|---|---|---|
| 105414 | 4/1984 | European Pat. Off. | 606/157 |
| 975006 | 11/1982 | U.S.S.R. | 606/139 |

*Primary Examiner*—Tamara L. Graysay
*Attorney, Agent, or Firm*—Wheeler & Kromholz

[57] ABSTRACT

A self locking suture lock having a first suture thread opening in which the thread is secured before the surgical stitch and a cone shaped second stitch lock opening that is larger at the front side than at the back side, and designed to receive suture thread in only one direction, thereby locking it against withdrawal after the stitch to complete and lock it without the need for a surgical knot. A tongue in the second opening will allow passage through the cone shaped second opening from front side to back side but not allow passage from back to side to front side or pulling out of second opening once threaded. The front side of the self locking suture may be distinctively colored so that a surgeon will know which side of the suture lock will accept the suture thread. The first opening may take the form of a deformable slot, a pair of openings, or other forms. The tongue may engage the edge of the second opening, a slot, or other unidirectional lock structures.

5 Claims, 2 Drawing Sheets

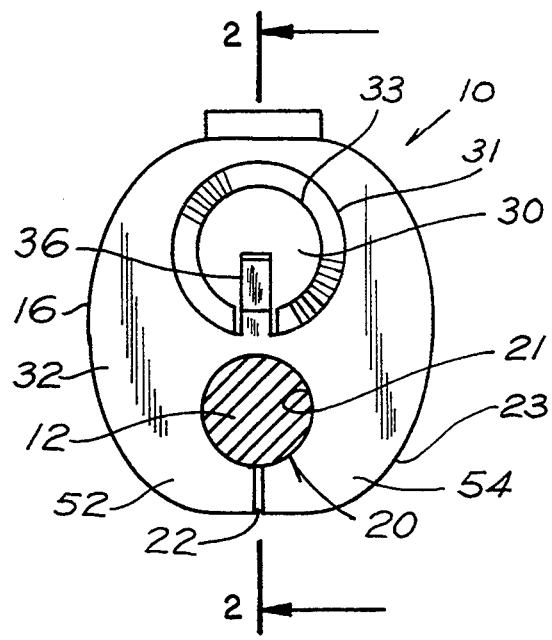
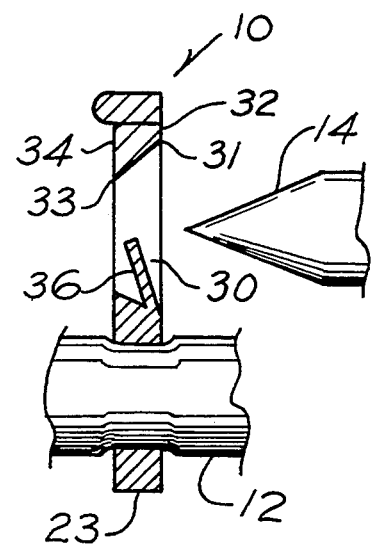
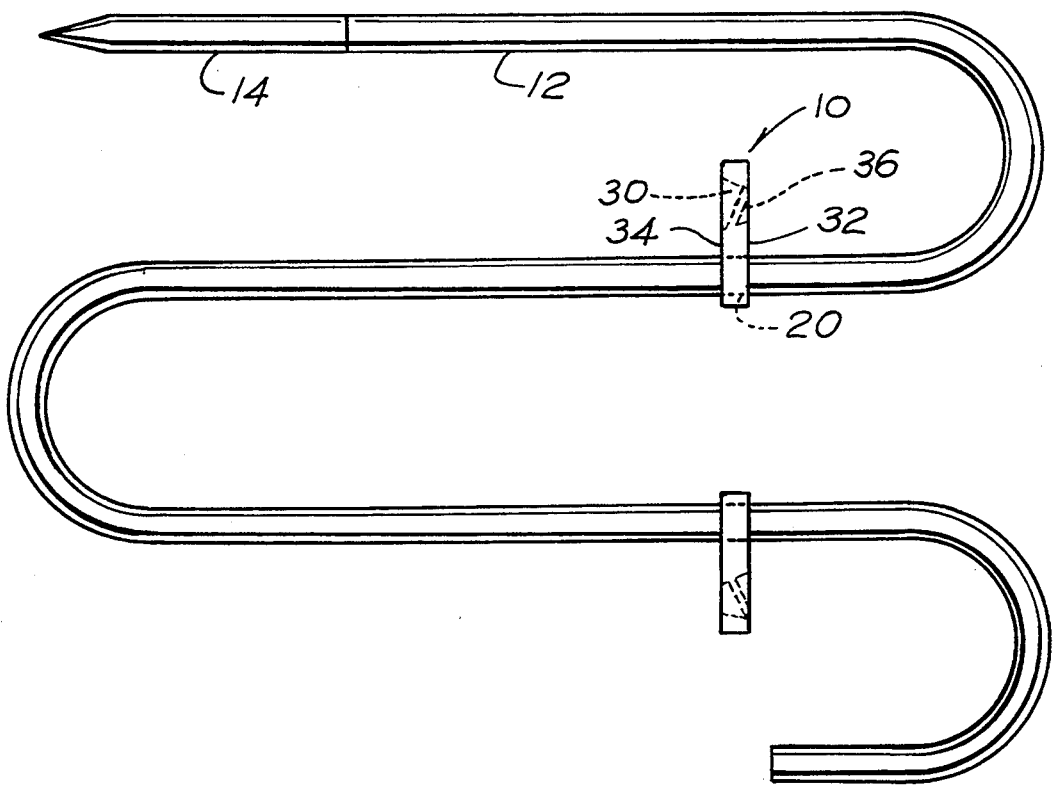

SELF LOCKING SUTURE LOCK

BACKGROUND OF THE INVENTION

The need for this invention arises from surgical practice, particularly surgical practice using laparoscopic instruments involving small incisions, with a television camera inserted in one of the incisions to view the field of the operation inside the patient and surgical instruments inserted in other incisions and manipulated from outside the patient's body using a TV screen visualization, usually enlarged, to guide the work.

Anything that can reduce the number of steps to be performed in such an operation can markedly reduce the stress, both on the patient and on the doctor. Surgeons performing such operations are under considerable stress because remote manipulation using TV for visualization, rather than seeing the site of the operation directly requires the learning of a great many techniques that are radically different from those performed when the surgical site is open to view. These include indirect hand-eye coordination, and cooperation between surgeons to place and secure sutures.

The placing of sutures during a laparoscopic procedure typically requires two surgeons to cooperate in a multi-step process performed with multiple surgical instruments to manipulate the needle and the suture and pass it back and forth from one to the other, cooperation in tieing the knot, etc. This invention arose from the difficulty of such manipulations.

SUMMARY OF THE INVENTION

The present invention relies primarily on a specialized lock having a body with two openings. The first opening is a suture lock opening which may receive the suture material freely and which may then secure the suture material to firmly attach the lock to the suture material at the desired distance from the suture needle. The needle is conventionally attached at the forward end of the suture. The location chosen for attachment of my lock is determined by the surgeon himself. The lock opening may take several forms. Illustrated are a deformable slot, a "weld", and a double opening. If the slot is used, an attaching tool (not shown) which may be plier-like is used to squeeze the lock, deforming the lock material around the suture after the lock is placed on the suture, to permanently fix the lock at the selected distance from the suture needle. If desired, a knot may be made in the suture to prevent movement of the lock beyond the desired location, a heat or solvent "weld" may be made, or the suture lock may be a plurality of openings shaped and oriented so that a suture may freely pass through but is held stationary when under tension, in a manner known in seat belts and other strap tension devices, but not known in surgical practice. This may be done initially, before the suture is used in a surgical procedure or passed through the laparoscopic tube to the site of a laparascopic operation. Later, added locks may be placed on the suture as suturing progresses, reducing the number of sutures that must be introduced to the operative site. The suture needle is then brought through the tissue to be sutured in the conventional way, after which the suture needle is passed through the second stitch lock opening in the suture lock.

Passage through the second or stitch lock opening is facilitated by making the opening in a highly visible color such as white, and by forming the opening with a cone-shaped approach to help guide the suture needle through the opening. The exit opening, in contrast, is little larger than the diameter of the suture itself so that it is neither very visible nor very approachable by the suture needle, to guard against the mistake of insertion in the wrong direction.

Within the stitch lock opening a flexible tongue projects into the opening for the suture and is inclined in the direction that the suture needle follows when it is inserted first into the large cone-shaped approach opening to later pass through the smaller exit opening. This flexible tongue freely allows the suture to pass, deflecting the tongue in the process, but the springiness of the tongue and the engagement of the tongue edge with the suture prevent withdrawal of the suture. The suture is under tension, so the pull deflects the tongue upward in the opening, jamming the suture against the side of the opening.

Desirably the flexible suture material that trails from the attached needle may be braided in a known way to have a very slight roughness to the surface in the direction from the end of the suture toward the needle, but to be smooth in the direction from needle to the end of the suture. Such suture material is known and is particularly appropriate for use with my novel lock because the flexible tongue can grip the suture even more firmly if it is of this character. It is also possible to design the channel for the suture to deviate around the end of the tongue. In this embodiment of the lock this action is enhanced by relieving the wall of the suture opening to allow further deflection of the tongue in a partial loop of the suture, increasing the locking force and angle of action. In either embodiment the deflection of the tongue when the suture is pulled through the channel in the correct direction opens the channel, whereas the passage of the suture around the end of the tongue, and through the deflection in the suture channel in one embodiment, pulls the tongue against the wall of the channel when the suture is stressed in the other direction, locking it firmly into place without any surgical knot, though such a knot may be added at the surgeon's discretion.

An additional advantage of my suture lock is that after the first stitch has been locked into place as described, the needle end of the suture remains free. A second suture lock may be placed on the suture at a suitable distance from the first suture lock and clamped into place on the suture after which the suture procedure can be repeated by passing the suture needle through additional tissue and again inserting the needle in the approach passage of the second suture lock, passing it through and pulling it tight. This second stitch is now locked into place but only a single piece of suture material has been used, eliminating the additional steps of removing the first suture needle and the remaining suture material from the wound, introducing a second suture and suture needle, etc. The number of sutures possible depends on suture length and on the location of the needed stitches. Thus many steps have been eliminated. These include at least the steps of cooperating to loop the suture about a clamping instrument, and then the two surgeons cooperating to pull the ends of the suture to tighten a knot, and in many cases the steps of introducing new sutures are also reduced.

Thus my improved suture lock eliminates a number of complex knot tieing steps and in the right circumstances can reduce the number of sutures required to be introduced to the surgical site, further reducing the number of steps to be performed by the surgeons and reducing the complexity of those steps so that the manipulations become easier. It is always an advantage to make the surgical manipulations easier, both to reduce stress on the surgeon and to reduce the possibility that the instruments or the needle will penetrate where they are not wanted. Simpler manipulation assists in this goal.

These and other benefits of the present invention will become apparent from the following detailed description thereof taken in conjunction with accompanying drawings.

DESCRIPTION OF THE DRAWINGS

FIG. 1 is a front elevational view of the invention.

FIG. 2 is a cross-sectional view of the invention on line 2—2 of FIG. 1.

FIG. 3 is a perspective view of the invention, suture thread, and a suture needle.

DETAILED DESCRIPTION

Figure 4:
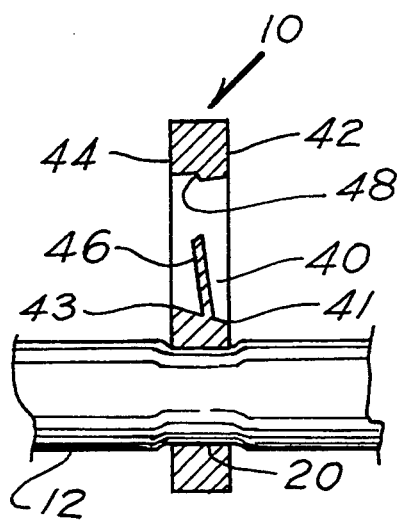
FIG. 4 is a cross-sectional view of an alternative embodiment of the invention on line 2—2 of FIG. 1.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Referring to FIG. 1, the self locking suture lock 10 includes a body 16 having a first suture lock opening 20, a second stitch lock opening 30, a front side 32, and a back side 34. The second opening 30 is cone shaped, with the diameter of the second opening 30 at edge 31 on the front side 32 being larger than the diameter of the second opening 30 at edge 33 on the back side 34. The diameter of the second opening 30 on the back side 34 is only slightly larger than the diameter of suture thread 12.

Referring also to FIG. 2, the area on the front side 32 of the body 16 around the second opening 30 between edges 31 and 33 may be colored differently than the rest of the body 16 in order to distinctly mark the difference between the front side 32 and the back side 34. This is so that the surgeon may distinguish the front side 32 from the back side 34 of the suture lock body 16. This helps to prevent the surgeon from inserting the suture thread 12 into the second opening 30 in the wrong direction, as does the tongue orientation.

As shown in FIG. 1, the first opening 20 has a circular thread opening 21 and a slot 22. The slot 22 projects inwardly from edge 23 to meet thread opening 21, creating two arms 52 and 54 that are separated by slot 22. The diameter of thread opening 21 is slightly smaller than the diameter of suture thread 12 (FIG. 2).

Suture thread 12 is threaded through thread opening 21. Following that, an attaching tool is used to clamp arms 52 and 54 together. The material that the self locking suture 10 is formed from is deformable so that when the arms 52 and 54 are compressed together with an attaching tool or some other device, the diameter of thread opening 21 shrinks, clamping the body 16 to suture thread 12 and locking it in place on suture thread 12. The clamping of the suture thread 12 in the thread opening 21 completes the first step of a suture.

The tongue 36 in the second opening 30 is a resilient piece of body material that is connected integrally to the body 16 at the outer edge 31 of the second opening 30 nearer to the front side 32 than to the back side 34. The tongue 36 extends inwardly from the outer edge 31 at an angle toward the back side 34.

Figure 5:
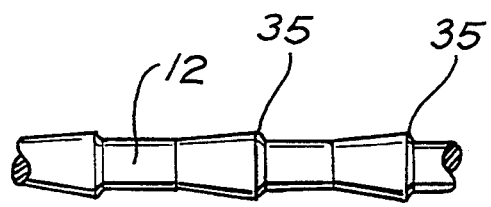
FIG. 5 is a side view of a suture showing a ridged structure, not to scale.

The cone shape of the second opening 30 creates an approach that allows for easy passage of the suture needle 14 and suture thread 12 through the second opening 30 from the front side 32 to the back side 34. This deflects tongue 36 further toward the back side 34. The deflection of tongue 36 thus allows passage of the suture needle 14 and suture thread 12 through the second opening 30 from the front side 32 to the back side 34, but prevents passage of the suture thread 12 back through the second opening 30 from back side 34 to front side 32. The suture thread 12 is locked into the self locking suture lock 10 in this manner. Desirably the suture thread 12 may have tiny ridges 35 that are more inclined from the direction along thread 12 on the slope toward the tail of the thread than toward the needle (FIG. 5).

The self locking suture lock 10 works as follows. First, a self locking suture lock 10 is attached as previously described to a strand of suture thread 12 at a position determined by the surgeon, often at the end remote from the needle. A conventional straight or curved suture needle 14 is connected permanently to the free end of the suture thread 12. The combined suture and lock are introduced to the operative site, through a laparoscopic tube if the operation is laparoscopic. Second, the suture needle 14 and suture thread 12 are brought through the tissue to be sutured in the conventional manner. Third, the suture needle 14 and suture thread 12 are threaded through the second stitch lock opening 30 of the self locking suture 10 from the front side 32 to the back side 34 and pulled as tight as needed. The suture is then complete, without the need for a surgical knot, and also without the need for a second surgeon.

Additionally, since the suture thread 12 remains free at the end where the suture needle 14 is attached, another self locking suture lock 10 may be introduced to the operative site, if necessary through a laparoscopic tube, and clamped at a desired position on the same suture thread 12. Following that, another stitch may be made and locked in the same manner as described above. The number of stitches is limited only by the length of thread 12 and the length of thread in each stitch.

Figure 6:
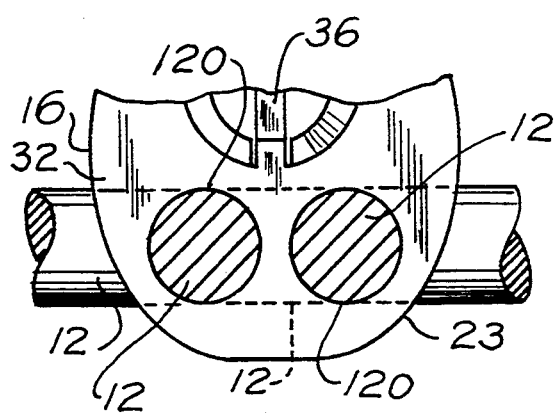
FIG. 6 is a fragmentary view like FIG. 1 showing an alternate embodiment.
Figure 7:
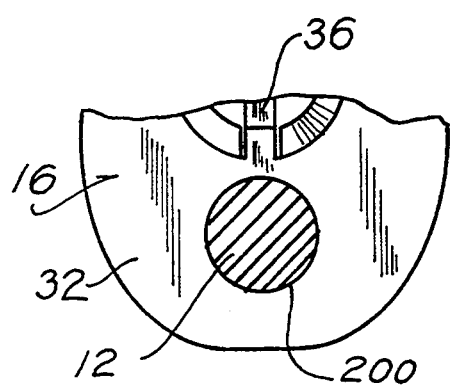
FIG. 7 is a fragmentary view like FIG. 1 showing an alternate embodiment.

Referring to FIG. 4, an alternative embodiment of the self locking suture 10' is shown. The first opening 20 may be identical to the first embodiment or as shown in FIG. 6 or 7. The alternative second opening 40 has a tongue 46, an outer edge 41, inner edge 43 and a notch 48. As in the first embodiment, the diameter of the front side 42 is larger than the diameter of the back side 44, and the tongue 46 extends inwardly from outer edge 41 toward the back side 44. On the cone shaped margin of opening 40 between edges 41 and 43 is formed notch 48. Tongue 46 extends resiliently across alternative second opening 40 to cause thread 12 to engage notch 48 when tongue 46 is deflected by suture thread 12. When suture thread 12 is passed through alternative second opening 40, suture thread 12 deflects tongue 46 away from notch 48 toward back side 44. Thus suture thread 12 deviates around tongue 46. When suture thread 12 is pulled with the needle 14 through alternative second opening 40 from front side 42 to back side 44, suture thread 12 may pass freely. When suture thread 12 is pulled in any other direction, most notably from back side 44 to front side 42, tongue 46 is pulled or pushed toward notch 48, locking suture thread 12 in the self locking suture 10', again without the need for a surgical knot, or for a second surgeon to assist in tying if the operation is laparascopic.

Front side 42 of the opening 40 is desirably colored differently than the remainder of the self locking suture lock 10', to facilitate distinguishing between front side 42 and back side 44.

FIG. 6 shows an alternative first opening that takes the form of a pair of holes 120 with sharp edges where holes 120 meet front side 32 and back side 34 of body 16 so that when thread 12 passes through both holes 120, tension on the suture holds thread 12 against movement.

FIG. 7 shows a further embodiment in which thread 12 is locked in first opening 20 by a solvent weld or heat weld 200 in a known manner. Sutures are commonly made of material capable of such treatment.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A molded plastic one-piece self locking suture lock to be used with surgical suture thread and a suture needle, said self locking suture lock comprising:

a body having a front side, a back side, a first edge, a thread retaining opening, and a stitch lock opening;

said thread retaining opening having a thread opening slightly smaller in diameter than said suture thread and a slot extending outwardly from said thread opening to said first edge;

said stitch lock opening being cone-shaped, having an outer edge, and having a larger diameter on said front side and a smaller diameter on said back side;

said body having an integral tongue connected to said outer edge of the stitch lock opening near said front side and extending diametrically at an angle from said front side toward said back side.

2. The self locking suture lock of claim 1 in which said front side of said body is distinctively colored around said stitch lock opening.

3. The self locking suture lock of claim 1 further comprising:

a notch in said outer edge of said stitch lock opening, substantially diametrically opposed to the point of connection between said tongue and said outer edge.

4. The self locking suture lock of claim 1 in which said body has arms adjacent said thread retaining opening for clamping suture thread in said thread retaining opening.

5. A one-piece self locking suture lock to be used with surgical suture thread and a suture needle, said self locking suture lock comprising:

a body having a front side, a back side, and a first edge;

said body having a first opening, said first opening having a thread opening slightly smaller in diameter than said suture thread, and a slot extending outwardly from said thread opening to said first edge;

said body having a cone shaped second opening with its larger diameter on said front side and a smaller diameter on said back side and approaching said notch;

said second opening having a tongue, an outer edge, and a notch;

said tongue connected to said outer edge near said front side, and extending inwardly at an angle from said front side toward said back side;

said front side of said body being distinctively colored in an area around said second opening.

* * * * *